US009682911B2

(12) United States Patent
Yofu et al.

(10) Patent No.: US 9,682,911 B2
(45) Date of Patent: Jun. 20, 2017

(54) METHOD FOR PRODUCING α-HALOGENOACETOPHENON COMPOUND, AND α-BROMOACETOPHENON COMPOUND

(71) Applicant: FUJIFILM Corporation, Tokyo (JP)

(72) Inventors: Katsuyuki Yofu, Kanagawa (JP); Akihito Amao, Kanagawa (JP); Katsuhiro Shimono, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/075,744

(22) Filed: Mar. 21, 2016

(65) Prior Publication Data

US 2016/0200654 A1 Jul. 14, 2016

Related U.S. Application Data

(63) Continuation of application No. PCT/JP2014/073861, filed on Sep. 10, 2014.

(30) Foreign Application Priority Data

Sep. 30, 2013 (JP) .................. 2013-204464
Dec. 26, 2013 (JP) .................. 2013-270176
May 15, 2014 (JP) .................. 2014-101627

(51) Int. Cl.
C07C 45/46 (2006.01)
C07C 67/29 (2006.01)
C07C 319/20 (2006.01)
C07C 49/84 (2006.01)

(52) U.S. Cl.
CPC .............. *C07C 45/46* (2013.01); *C07C 49/84* (2013.01); *C07C 67/29* (2013.01); *C07C 319/20* (2013.01)

(58) Field of Classification Search
CPC ........ C07C 45/46; C07C 67/29; C07C 319/20
USPC .................................. 568/308, 322
See application file for complete search history.

(56) References Cited

U.S. PATENT DOCUMENTS

| 4,347,111 A * | 8/1982 | Gehlhaus | C07C 45/004 430/923 |
| 5,744,512 A * | 4/1998 | Kohler | C08F 2/50 522/34 |
| 7,482,392 B2 * | 1/2009 | Norcini | C07C 45/46 522/42 |

FOREIGN PATENT DOCUMENTS

| CN | 101811951 A | 8/2010 |
| JP | S53-144539 | 12/1978 |
| JP | H06-228218 A | 8/1994 |
| JP | H10-175908 A | 6/1998 |
| JP | H10-330317 A | 12/1998 |
| JP | 2000-186242 A | 7/2000 |
| JP | 2012-051927 A | 3/2012 |
| JP | 2012-087113 A | 5/2012 |

OTHER PUBLICATIONS

International Search Report of PCT/JP2014/073861 mailed Nov. 18, 2014.
Written Opinion of PCT/JP2014/073861 mailed Nov. 18, 2014.
The Fifth Series of Experimental Chemistry, The Synthesis of Organic Compound III, vol. 15, The Chemical Society of Japan.
The extended European search report issued by the European Patent Office on Sep. 8, 2016, which corresponds to European Patent Application No. 14849333.1-1451 and is related to U.S. Appl. No. 15/075,744.
The First Office Action issued by the State Intellectual Property Office of People's Republic of China on Sep. 29, 2016, which corresponds to Chinese Patent Application No. 201480053921.2 and is related to U.S. Appl. No. 15/075,744; with English language translation.
An Office Action "Notification of Reasons for Refusal" issued by the Japanese Patent Office on Sep. 27, 2016, which corresponds to Japanese Patent Application No. 2015-539085 and is related to U.S. Appl. No. 15/075,744; with English language translation.

* cited by examiner

*Primary Examiner* — Sikarl Witherspoon
(74) *Attorney, Agent, or Firm* — Studebaker & Brackett PC

(57) ABSTRACT

A method for producing an α-halogenoacetophenon compound includes reacting a specific α-halogenocarboxylic halide compound and a specific phenyl compound in the presence of a Lewis acid in a solvent, in which the α-halogenoacetophenon compound and the phenyl compound are reacted with each other in a molar ratio of the Lewis acid to the phenyl compound represented below.

2≤Lewis acid/phenyl compound≤6

16 Claims, No Drawings

METHOD FOR PRODUCING α-HALOGENOACETOPHENON COMPOUND, AND α-BROMOACETOPHENON COMPOUND

CROSS-REFERENCE TO RELATED APPLICATIONS

This application is a Continuation of PCT International Application No. PCT/JP2014/073861 filed on Sep. 10, 2014, which claims priority under 35 U.S.C §119(a) to Japanese Patent Application No. 2013-204464 filed on Sep. 30, 2013, Japanese Patent Application No. 2013-270176 filed on Dec. 26, 2013, and Japanese Patent Application No. 2014-101627 filed on May 15, 2014. Each of the above applications is hereby expressly incorporated by reference, in its entirety, into the present application.

BACKGROUND OF THE INVENTION

1. Field of the Invention

The present invention relates to a method for producing an α-halogenoacetophenon compound and an α-bromoacetophenon compound.

2. Description of the Related Art

As a polymerization initiator of a polymerizable compound having an ethylenically unsaturated bond, an α-hydroxyacetophenone-based photopolymerization initiator has been known. The α-hydroxyacetophenone-based photopolymerization initiator is generally obtained by acylating a phenyl compound using carboxylic halide such as isobutyric acid chloride, in the presence of a Lewis acid, brominating a carbon atom of the acyl group, and substituting bromine atom to a hydroxyl group (for example, JP1994-228218A (JP-H06-228218A)).

In addition, JP2012-51927A discloses acylating diphenyl ether using α-bromoisobutyryl bromide. According to this method, it is possible to omit a bromination after acylation as disclosed in JP1994-228218A (JP-H06-228218A).

SUMMARY OF THE INVENTION

However, in the method disclosed in JP1994-228218A (JP-H06-228218A), a portion (for example, a portion of a benzene ring-forming carbon atoms) other than a desired portion at the time of brominating is also brominated to a certain degree, and there is a limit to improve the purity of the obtained photopolymerization initiator. Therefore, in order to obtain a desired compound with high purity in a brominating method disclosed in JP1994-228218A (JP-H06-228218A), a purification process after reaction is essential.

In addition, JP2012-51927A discloses obtaining a synthetic intermediate by acylating diphenyl ether using α-bromoisobutyryl bromide. However, reaction selectivity to the acylated portion is not sufficient, and a synthetic intermediate with high purity may not be obtained. A purification process after the acylation reaction is essential to obtain the synthetic intermediate with high purity.

In general, if the melting point of a desired compound is sufficiently high and the compound is in a solid state at room temperature or at a temperature lower than room temperature, a desired compound can be purified in a recrystallization method to a higher degree. However, in case the melting point of the desired compound is low, high purification in such a general method is difficult.

There are various uses of the photopolymerization initiator. In addition to the use as a curing agent component such as paint, an adhesive, an optical film, and a solder resist material, the use which requires solubility to a solvent including water expands. For example, in case a photopolymerization initiator is used as a curable ink component for an ink-jet printer, it is required to impart hydrophilicity by increasing the polarity.

An object of the invention is to provide a method for manufacturing an α-halogenoacetophenon compound useful as a synthetic intermediate of a photopolymerization initiator having a specific polar group with excellent reaction purity.

The object of the invention is solved by the means below.

[1]

A method for producing an α-halogenoacetophenon compound represented by Formula (3) below, including: reacting an α-halogenocarboxylic halide compound represented by Formula (1) below and a phenyl compound represented by Formula (2) in the presence of a Lewis acid in a solvent, in which the α-halogenocarboxylic halide compound and the phenyl compound represented by Formula (2) are reacted with each other in a molar ratio of the Lewis acid to the phenyl compound represented below, 2≤Lewis acid/phenyl compound≤6.

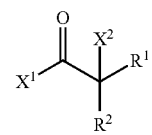

Formula (1)

In Formula (1), each of $R^1$ and $R^2$ independently represents an alkyl group, and each of $X^1$ and $X^2$ independently represents a halogen atom.

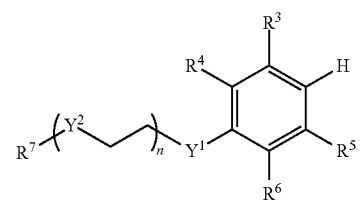

Formula (2)

In Formula (2), each of $R^3$ to $R^6$ independently represents a hydrogen atom or a substituent, $R^7$ represents a hydrogen atom, an alkyl group, an acyl group, or a trialkylsilyl group, each of $Y^1$ and $Y^2$ independently represents an oxygen atom or a sulfur atom, and n represents an integer of 1 to 3.

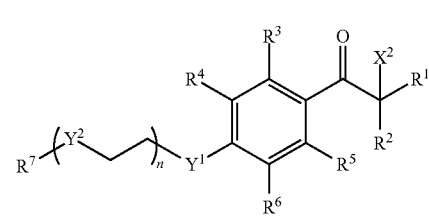

Formula (3)

In Formula (3), $R^1$, $R^2$, and $X^2$ respectively have the same meanings as $R^1$, $R^2$, and $X^2$ in Formula (1), and $R^3$ to $R^7$, $Y^1$, $Y^2$, and n respectively have the same meanings as $R^3$ to $R^7$, $Y^1$, $Y^2$, and n in Formula (2).

[2]
The method for producing an α-halogenoacetophenon compound according to [1], in which, in Formula (1), $X^1$ represents a bromine atom.

[3]
The method for producing an α-halogenoacetophenon compound according to [2], in which, in Formula (1), $R^1$ and $R^2$ are methyl.

[4]
The method for producing an α-halogenoacetophenon compound according to any one of [1] to [3], in which aluminium (III) chloride is used as the Lewis acid.

[5]
The method for producing an α-halogenoacetophenon compound according to any one of [1] to [4], in which $R^7$ in Formulae (2) and (3) is an alkylcarbonyl group or an arylcarbonyl group.

[6]
The method for producing an α-halogenoacetophenon compound according to any one of [1] to [5], in which n in Formulae (2) and (3) is 2.

[7]
The method for producing an α-halogenoacetophenon compound according to any one of [1] to [6], in which at least one selected from dichloromethane, chlorobenzene, sulfolane, ethyl acetate, acetonitrile, 1,3,5-trimethylbenzene, methyl ethyl ketone, and o-dichlorobenzene is used as the solvent.

[8]
The method for producing an α-halogenoacetophenon compound according to any one of [1] to [7], in which, at least one selected from dichloromethane, chlorobenzene, and o-dichlorobenzene is used as the solvent.

[9]
The method for producing an α-halogenoacetophenon compound according to any one of [1] to [8], in which o-dichlorobenzene is used as the solvent.

[10]
The method for producing an α-halogenoacetophenon compound according to [9], in which the α-halogenocarboxylic halide compound and the phenyl compound represented by Formula (2) are reacted with each other in a molar ratio of the o-dichlorobenzene to the phenyl compound represented below.

5≤o-dichlorobenzene/phenyl compound≤20

[11]
The method for producing an α-halogenoacetophenon compound according to [9] or [10], in which aluminium (III) chloride as the Lewis acid and the α-halogenocarboxylic halide compound represented by Formula (1) are mixed with each other, in the o-dichlorobenzene, and the phenyl compound is subsequently mixed.

[12]
The method for producing an α-halogenoacetophenon compound according to any one of [1] to [11], in which the α-halogenocarboxylic halide compound and the phenyl compound are reacted under a temperature condition of 30° C. or lower.

[13]
An α-bromoacetophenon compound represented by Formula (6) below.

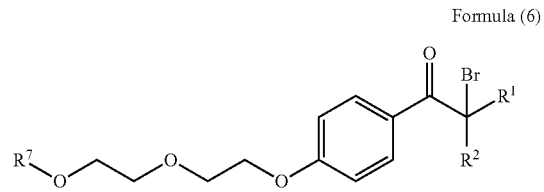

Formula (6)

In Formula (6), each of $R^1$ and $R^2$ independently represents an alkyl group, and $R^7$ represents a hydrogen atom, an alkyl group, an acyl group, or a trialkylsilyl group.

[14]
The α-bromoacetophenon compound according to [13], in which, in Formula (6), $R^1$ and $R^2$ are methyl, and $R^7$ is a hydrogen atom or acetyl.

In the producing method according to the invention, an excessive amount of a Lewis acid is used in a specific phenyl compound having a polar substituent. In this manner, an acyl group derived from the α-halogenocarboxylic halide can be introduced at a para position to a bond portion of the substituent of the specific phenyl compound in a moderate temperature condition with an extremely high position selectivity. That is, the α-halogenoacetophenon compound can be obtained with a high reaction purity by the producing method according to the invention, and thus the α-hydroxyacetophenone compound which is useful as the photopolymerization initiator can be obtained with a high reaction purity.

In addition, the producing method according to the invention does not generally require a refinement process such as recrystallization, and thus the producing method according to the invention is particularly useful in case a melting point of the desired α-halogenoacetophenon compound or the introduced α-hydroxyacetophenone compound is low, and refinement by recrystallization is difficult.

DESCRIPTION OF THE PREFERRED EMBODIMENTS

The producing method of the α-halogenoacetophenon compound according to the invention (hereinafter, simply referred to "producing method according to the invention") is described in detail.

In the producing method according to the invention, as a starting material, a specific α-halogenocarboxylic halide compound and a specific phenyl compound having a polar group are used and are reacted in the presence of a specific amount of a Lewis acid in the solvent.

[α-halogenocarboxylic halide Compound]
The α-halogenocarboxylic halide compound used in the producing method according to the invention is represented by Formula (1) below.

Formula (1)

In Formula (1), each of $R^1$ and $R^2$ independently represents an alkyl group. Each of $R^1$ and $R^2$ may be a straight chain or may be branched. Each of $R^1$ and $R^2$ is an alkyl group having preferably 1 to 10 carbon atoms, more preferably 1 to 5 carbon atoms, still more preferably 1 to 3 carbon atoms, and it is still more preferable that each of $R^1$ and $R^2$ is methyl or ethyl.

In addition, $R^1$ and $R^2$ may be connected to each other to form a ring. The group having a ring structure which is formed by connecting $R^1$ and $R^2$ is preferably a cycloalkyl group. The group is more preferably a cycloalkyl group having 3 to 10 carbon atoms and still more preferably a cycloalkyl group having 4 to 8 carbon atoms. Specifically, cycloheptyl or cyclohexyl is preferable.

In Formula (1), each of $X^1$ and $X^2$ independently represents a halogen atom. Specifically, each of $X^1$ and $X^2$ is a bromine atom, a chlorine atom, an iodine atom, or a fluorine atom, and more preferably a bromine atom or a chlorine atom. Among these, in view of yield and purity, it is preferable that $X^1$ is a bromine atom, it is more preferable that $X^1$ is a bromine atom and $X^2$ is a bromine atom or a chlorine atom, and it is still more preferable that both of $X^1$ and $X^2$ are bromine atoms.

Specific examples of the α-halogenocarboxylic halide compound that can be used in the invention are provided below, but the invention is not limited thereto.

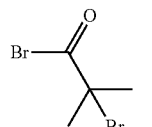
(1)-1

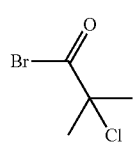
(1)-2

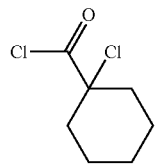
(1)-3

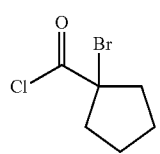
(1)-4

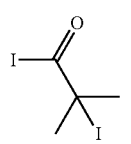
(1)-5

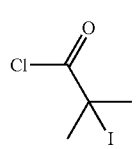
(1)-6

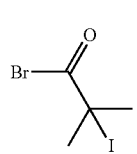
(1)-7

-continued

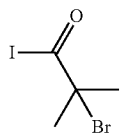
(1)-8

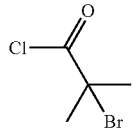
(1)-9

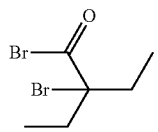
(1)-10

The α-halogenocarboxylic halide compound used in the invention can be synthesized in a usual way. For example, the α-halogenocarboxylic halide compound can be synthesized by causing halogen such as chlorine, bromine, and iodine to act on the carboxylic halide compound.

The α-halogenocarboxylic halide compound represented by Formula (1) becomes an electrophilic reagent in the presence of a Lewis acid.

The usage amount of the α-halogenocarboxylic halide compound represented by Formula (1) in the producing method according to the invention is preferably 1.0 to 2.0, more preferably 1.0 to 1.5, and still more preferably 1.0 to 1.3 by a molar ratio (α-halogenocarboxylic halide compound/phenyl compound) to a phenyl compound described below.

[Phenyl Compound]

The phenyl compound used in the producing method according to the invention is represented by Formula (2) below.

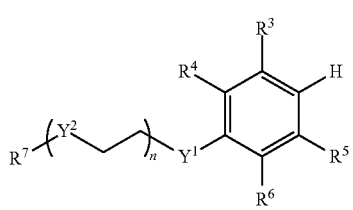
Formula (2)

In Formula (2), each of $R^3$ to $R^6$ independently represents a hydrogen atom or a substituent. At least one of $R^3$ to $R^6$ is preferably a hydrogen atom. In addition, it is preferable that two or more of $R^3$ to $R^6$ are hydrogen atoms, and, in this case, at least one or both of $R^3$ and $R^5$ are more preferably hydrogen atoms. In addition, it is more preferable that three or more of $R^3$ to $R^6$ are hydrogen atoms, and, in this case, it is more preferable that $R^3$ and $R^5$ are hydrogen atoms. It is still more preferable that all of $R^3$ to $R^6$ are hydrogen atoms.

As described below, in the producing method according to the invention, it is possible to introduce an acyl group to a para position to —$Y^1$— in extremely high position selectivity even though an additive amount of the Lewis acid to the phenyl compound is considerably greater than an additive amount in the general Friedel-crafts acylation reaction. Further, this reaction progresses in a moderate temperature condition.

In case $R^3$ to $R^6$ are substituents, examples of the substituent include a group selected from an alkyl group (alkyl group having preferably 1 to 5 carbon atoms, more preferably 1 to 3 carbon atoms, still more preferably 1 or 2 carbon atoms), a halogen atom (for example, a fluorine atom, a chlorine atom, a bromine atom, and an iodine atom), an amino group, a hydroxy group, a cyano group, a nitro group, a carboxyl group, a sulfo group, a sulfonyl group, a phosphonyl group, a boric acid group, an alkoxy group, and an amide group. Among these, methyl, ethyl, or a halogen atom is preferable.

In Formula (2), $R^7$ represents a hydrogen atom, an alkyl group, an acyl group, or a trialkylsilyl group.

In case $R^7$ is alkyl, $R^7$ may be a straight chain, may be branched, or may have a substituent. This alkyl group has preferably 1 to 10 carbon atoms and more preferably 1 to 7 carbon atoms. Specifically, for example, methyl, ethyl, propyl, isopropyl, t-butyl, methoxymethyl, and ethoxyethyl, and benzyl, p-methoxybenzyl, and phenethyl which are aralkyl groups are preferable, and methyl, t-butyl, and benzyl are more preferable.

In case $R^7$ is an acyl group, the number of carbon atoms is preferably 2 to 12. In case $R^7$ is an acyl group, an alkylcarbonyl group or an arylcarbonyl group is preferable.

In case $R^7$ is an alkylcarbonyl group, $R^7$ may be a straight chain or may be branched. This alkylcarbonyl group preferably has 2 to 11 carbon atoms, more preferably 2 to 6 carbon atoms, and still more preferably 2 to 4 carbon atoms. Specific examples include acetyl, propionyl, butyryl, isobutyryl, pivaloyl, and acryloyl.

In case $R^7$ is an arylcarbonyl group, the number of carbon atoms is preferably 7 to 21, more preferably 7 to 16, and still more preferably 7 to 13. Among these, benzoyl is preferable.

In case $R^7$ is a trialkylsilyl group, an alkyl group of a trialkylsilyl group may be a straight chain or may be branched. The alkyl group has preferably 1 to 10 carbon atoms, more preferably 1 to 6 carbon atoms, still and more preferably 1 to 4 carbon atoms. Specific examples thereof include trimethylsilyl, triethylsilyl, t-butyldimethylsilyl, and triisopropylsilyl, and trimethylsilyl is preferable.

In Formula (2), each of $Y^1$ and $Y^2$ independently represents an oxygen atom or a sulfur atom, and more preferably an oxygen atom.

In Formula (2), n is an integer of 1 to 3. In view of position selectivity of the Friedel-crafts acylation reaction described below, n is preferably 2 or 3. It is assumed that this is because, if n increases, steric hindrance increases such that para position selectivity increases. In addition, if n is 2 or 3, water solubility of the polymerization initiator such as the α-hydroxyacetophenone compound introduced from Formula (2) increases, and thus it is possible to obtain a suitable polymerization initiator as an aqueous initiator.

In addition, in view of a reaction yield, it is most preferable that n is 2. It is assumed that, if n increases, a Lewis acid coordinated with an alkylene oxide group increases, such that an amount of a Lewis acid contributing to the Friedel-crafts acylation reaction decreases.

Specific examples of the phenyl compound represented by Formula (2) used in the invention are provided below, but the invention is not limited thereto.

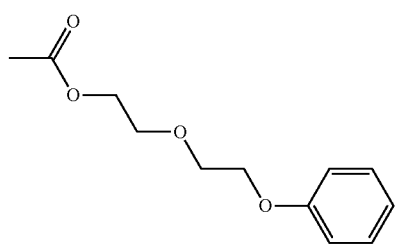
(2)-1

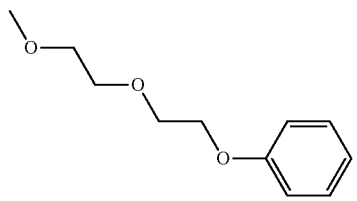
(2)-2

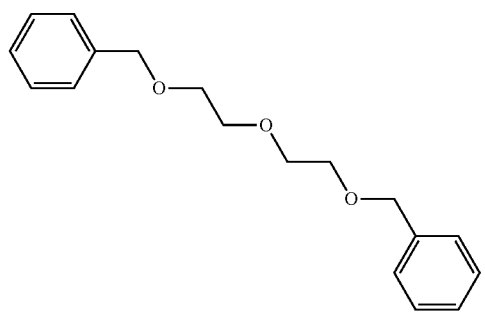
(2)-3

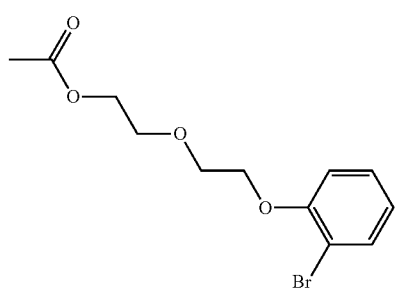
(2)-4

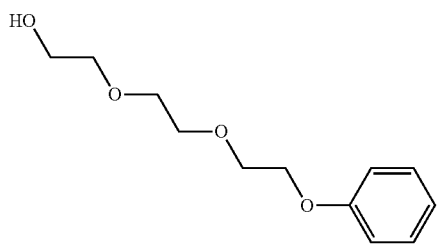
(2)-5

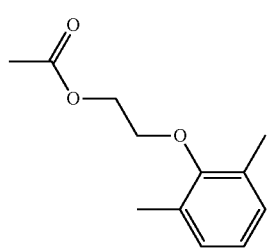
(2)-6

-continued

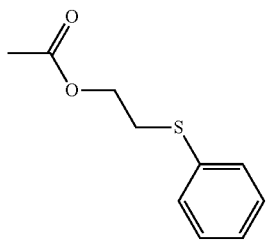
(2)-7

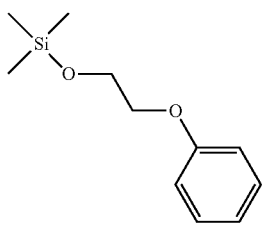
(2)-8

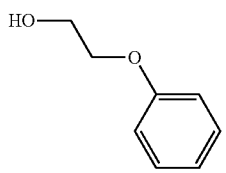
(2)-9

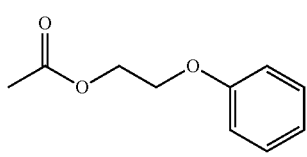
(2)-10

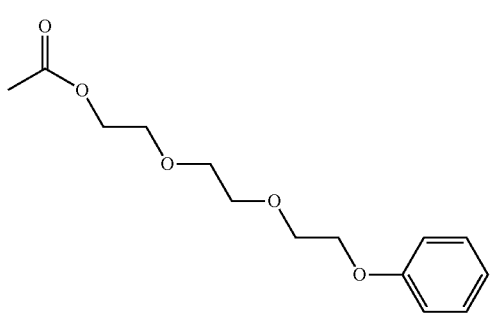
(2)-11

The phenyl compound used in the invention can be synthesized in a usual way. For example, in the case of an acetyl body, the phenyl compound can be obtained by the general acetylation reaction (mixing and heating alcohol and acetic anhydride corresponding to each other). In addition, in the case of a silyl body, the phenyl compound can be obtained in the general alcohol protection (mixing and heating alcohol and trialkylsilyl chloride corresponding to each other). For example, the compound (2)-8 can be synthesized in conformity with methods disclosed in J. Org. Chem, 1990, 55, 16, p. 4887-4892.

[Lewis Acid]

The Lewis acid used in the producing method according to the invention functions as a catalyst in the acylation reaction. That is, a halogen atom ($X^1$) is extracted from the α-halogenocarboxylic halide compound represented by Formula (1) above so as to generate an electrophilic reagent, and this electrophilic reagent acylates the phenyl compound. The extracted halogen atom is bonded to hydrogen and becomes a halogenated hydrogen.

The Lewis acid used in the invention is not particularly limited, but a Lewis acid that functions as a catalyst in an acylation reaction in a moderate temperature condition is preferable. For example, one or more types selected from aluminium (III) chloride, aluminium (III) bromide, iron (III) chloride, iron (III) bromide, titanium (IV) chloride, zinc (II) chloride, zinc (II) bromide, a boron trifluoride-diethyl ether complex, boron trichloride, and boron tribromide can be used. Among these, one or more types selected from aluminium (III) chloride, aluminium (III) bromide, iron (III) chloride, iron (III) bromide, zinc (II) chloride, and zinc (II) bromide are preferably used, and aluminium (III) chloride is more preferably used.

In the producing method according to the invention, the reaction is performed such that the ratio (molar ratio) of the Lewis acid and the phenyl compound in the solvent satisfies (A) below. Further, it is preferable that the reaction is performed such that the ratio satisfies (B) below, it is more preferable that the reaction is performed such that the ratio satisfies (C) below, and it is still more preferable that the reaction is performed such that the ratio satisfies (D) below.

$2.0 \leq$ Lewis acid/phenyl compound $\leq 6.0$ (A)

$2.2 \leq$ Lewis acid/phenyl compound $\leq 5.0$ (B)

$2.5 \leq$ Lewis acid/phenyl compound $\leq 4.0$ (C)

$2.7 \leq$ Lewis acid/phenyl compound $\leq 3.5$ (D)

The ratio above is considerably greater than the usage ratio of the Lewis acid which is used in the general Friedel-crafts acylation reaction.

The present inventors have recognized that an acyl group is not sufficiently introduced to a benzene ring, when the phenyl compound of Formula (2) above and the α-halogenocarboxylic halide compound of Formula (1) above are reacted with each other and a phenyl compound are acylated in the conditions of the general Friedel-crafts acylation reaction. The reason is not clear, but it is considered that a polar group included in the compound of Formula (2) forms a complex with the Lewis acid.

Also, the present inventors have reviewed the reaction condition in various ways and have found that an acyl group can be effectively introduced to a benzene ring of the phenyl compound at room temperature or at a moderate temperature condition which is lower than room temperature by reacting the phenyl compound and the α-halogenocarboxylic halide compound in the presence of the solvent and a large amount of Lewis acid. Furthermore, the present inventors have found that this acyl group is introduced to a para position (para position to a substitution position of $Y^1$) with extremely high position selectivity even though a large amount of the Lewis acid is used.

In general, if the acylation reaction is performed by increasing the amount of the Lewis acid, acyl groups are introduced to plural ring-forming carbon atoms of the phenyl compound, and thus it becomes difficult to obtain monoacylated body selectively. In practice, as described in examples below, if acylation is performed in the presence of the Lewis acid in the amount regulated by the invention by using benzene instead of the phenyl compound, a considerable amount of $Y^1$) benzene to which three or more acyl groups are introduced is generated in addition to benzene to which one acyl group is introduced and benzene to which two acyl groups are introduced.

The present inventors have found that the phenyl compound is not sufficiently acylated with the general additive amount of the Lewis acid in the acylation reaction at the time of acylation of the phenyl compound of Formula (2) but the acyl group can be introduced with effective and excellent para position (para position to a bond portion of $Y^1$) selectivity in the additive amount of the Lewis acid in which it is considered that it is difficult to introduce an acyl group with position selectivity by the common general knowledge in the related art, to complete the producing method according to the invention.

[Solvent]

The solvent used in the producing method according to the invention is not particularly limited, but an organic solvent is preferable. Examples thereof include at least one type selected from dichloromethane (methylene chloride), chlorobenzene, sulfolane, ethyl acetate, acetonitrile, 1,3,5-trimethylbenzene (mesitylene), methyl ethyl ketone, o-dichlorobenzene, m-dichlorobenzene, p-dichlorobenzene, bromobenzene, o-dibromobenzene, m-dibromobenzene, p-dibromobenzene, and 1,2-dichloroethane. Among these, at least one type selected from methylene chloride, chlorobenzene, sulfolane, ethyl acetate, acetonitrile, mesitylene, methyl ethyl ketone, and o-dichlorobenzene is preferably used, and at least one selected from methylene chloride, chlorobenzene, and o-dichlorobenzene is more preferably used. In addition, in view of preventing yield, purity, and the temperature dependence to reactivity, it is preferable to use o-dichlorobenzene or methylene chloride, and it is still more preferable to use o-dichlorobenzene.

The usage amount of the solvent is not particularly limited, but the usage amount is preferably 1 to 100 in the molar ratio with respect to 1 of a phenyl compound.

If o-dichlorobenzene is used as the solvent, it is preferable to perform reaction such that the molar ratio of o-dichlorobenzene and the phenyl compound is the molar ratio below. If the usage amount of the solvent is in the range of the molar ratio below, it is difficult that impurities in the reaction system precipitate and the solvent in a subsequent step can be distilled more effectively.

5≤o-dichlorobenzene/phenyl compound≤20

In the producing method according to the invention, the mixture sequence of the respective reaction components is not particularly limited, but it is preferable that the α-halogenocarboxylic halide compound and the Lewis acid come into contact with each other before the α-halogenocarboxylic halide compound and the phenyl compound come into contact with each other. In this manner, it is possible to enhance the acylation efficiency of the phenyl compound when the α-halogenocarboxylic halide compound can be caused to an electrophilic reagent more efficiently.

That is, in the producing method according to the invention, it is preferable to perform acylation reaction by mixing the Lewis acid and the α-halogenocarboxylic halide compound in the solvent and subsequently mixing the phenyl compound. It is more preferable to perform acylation reaction by mixing the Lewis acid, the α-halogenocarboxylic halide compound, and the phenyl compound in the solvent, in this sequence.

In view of increasing the purity of the compound of Formula (3) below, the reaction temperature in the producing method according to the invention is preferably 50° C. or lower, more preferably 40° C. or lower, and still more preferably 30° C. or lower. The lower limit of the reaction temperature is not particularly limited, but the lower limit is preferably −15° C. or higher and more preferably 0° C. or higher. In the producing method according to the invention, the acylation reaction can be caused to progress at room temperature or in a moderate temperature condition lower than room temperature, and thus the producing method according to the invention is suitable for the industrial production of the α-halogenoacetophenon compound.

In addition, in view of preventing side reaction, the reaction time may be short. Specifically, the reaction time is preferably within 10 hours and more preferably within 5 hours. In addition, in order to obtain a sufficient yield, the reaction time is preferably 0.5 hours or longer, more preferably 1 hour or longer, still more preferably 1.5 hours or longer, and particularly preferably 2 hours or longer.

The reaction temperature and the reaction time are a temperature and time from a point in which the solvent, the Lewis acid, the α-halogenocarboxylic halide compound of Formula (1), and the phenyl compound of Formula (2) are caused to coexist, to the completion of the reaction. In case each of the α-halogenocarboxylic halide compound of Formula (1) and the phenyl compound of Formula (2) are added dropwise to the solvent including the Lewis acid, the reaction temperature and the reaction time are a temperature and time from a drop addition start point of a material which is added last, to the completion of the reaction. In addition, in this specification, reaction in a specific temperature (for example, 50° C. or lower, 40° C. or lower, and 30° C. or lower) does not mean that all steps in the reaction have to be performed in the specific temperature, but means that an aspect in which muturing reaction (for example, muturing reaction after a dropwise addition is completed in a dropwise addition reaction) is performed out of the specific temperature range.

The α-halogenoacetophenon compound that can be obtained in the producing method according to the invention is represented by Formula (3) below.

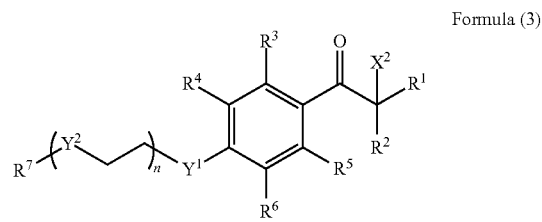

Formula (3)

In Formula (3), $R^1$, $R^2$, and $X^2$ have the same meaning as $R^1$, $R^2$, and $X^2$ in Formula (1) respectively, and preferable embodiments thereof are also the same. $R^3$ to $R^7$, $Y^1$, $Y^2$, and n have the same meaning as $R^3$ to $R^7$, $Y^1$, $Y^2$, and n in Formula (2) respectively, and preferable embodiments thereof are also the same.

The compound represented by Formula (3) above does not particularly limit the melting point, but it is preferable that the melting point is 50° C. or lower. For example, in case the compound represented by Formula (3) is a compound that is hardly refined by recrystallization such as a compound which is liquid in the range of 5° C. to 30° C., it is possible to obtain a compound represented by Formula (3) with high purity in the producing method according to the invention. In this specification, a compound which is liquid in the range of 5° C. to 30° C. means a compound in which crystals do not precipitate even if being left for one week in the atmosphere of 5° C. to 30° C.

The compound represented by Formula (3) above is preferably represented by Formula (6) below. The compound represented by Formula (6) below has appropriate polarity and affinity to an aqueous medium and thus the compound is particularly useful as a synthetic intermediate of the photopolymerization initiator that is dissolved in a solvent including water to be used.

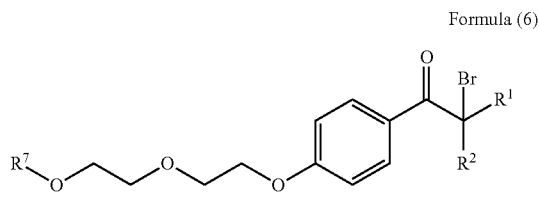

Formula (6)

In Formula (6), $R^1$ and $R^2$ have the same meaning as $R^1$ and $R^2$ in Formula (1) above, and preferable embodiments thereof are also the same. $R^7$ has the same meaning as $R^7$ of Formula (2) above, and preferable embodiments thereof are also the same. In Formula (6), $R^1$ and $R^2$ are preferably methyl. In addition, $R^7$ is preferably a hydrogen atom or acetyl.

Specific examples of the compound represented by Formula (3) are provided below, but the invention is not limited thereto.

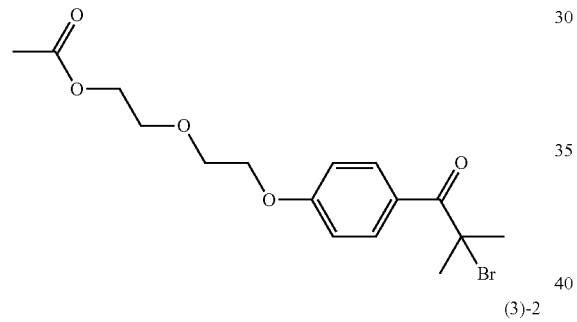

(3)-1

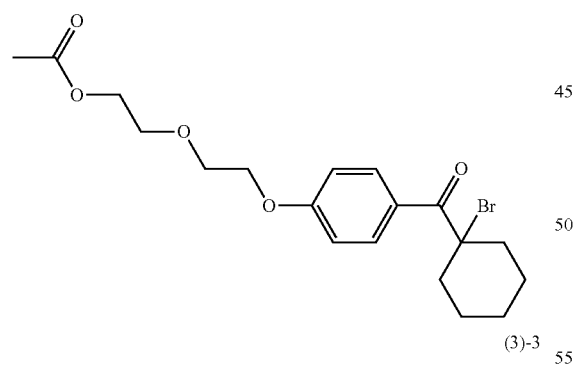

(3)-2

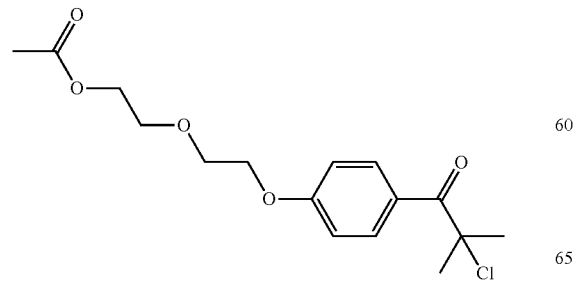

(3)-3

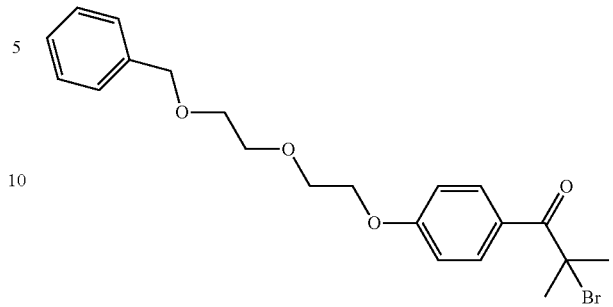

(3)-4

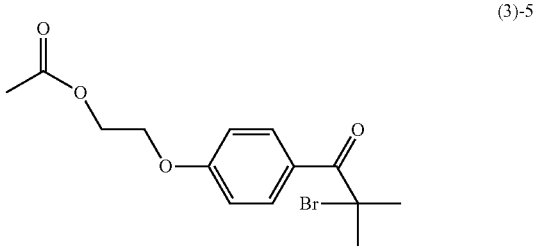

(3)-5

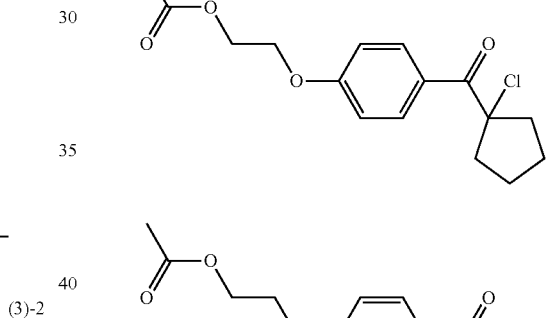

(3)-6

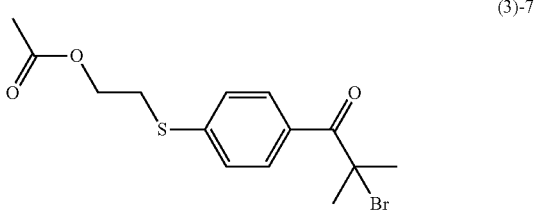

(3)-7

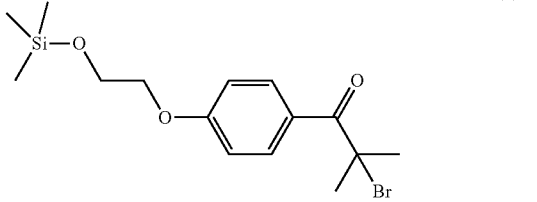

(3)-8

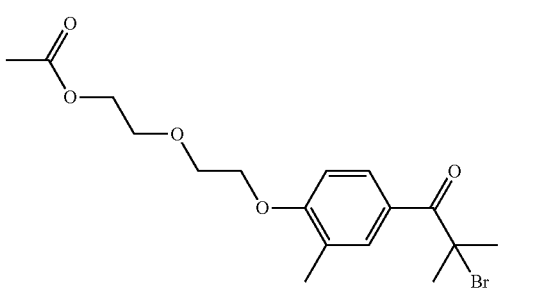

(3)-9

(3)-10
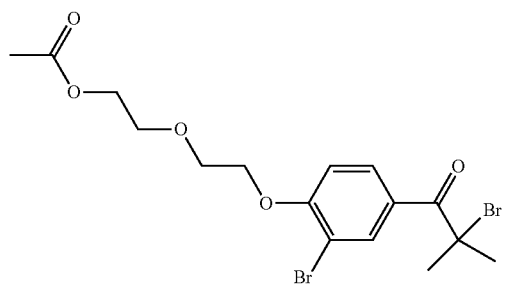
(3)-11
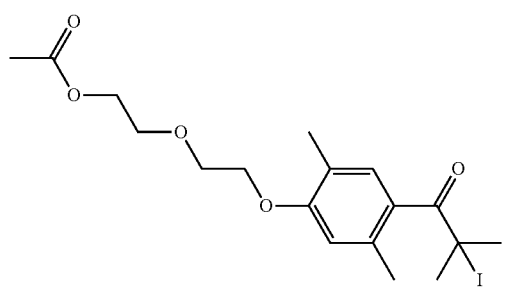
(3)-12
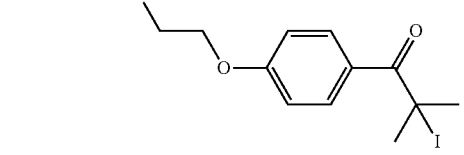
(3)-13
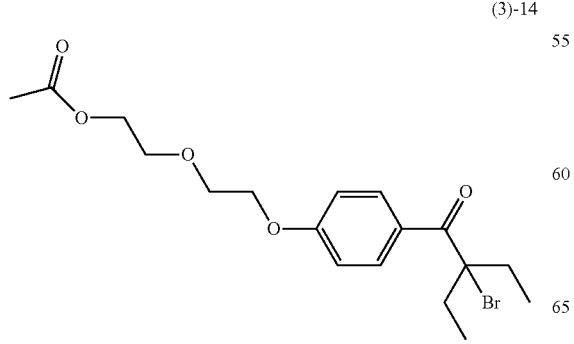
(3)-14
(3)-15
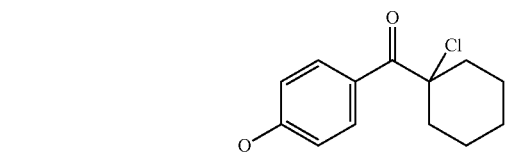
(3)-16
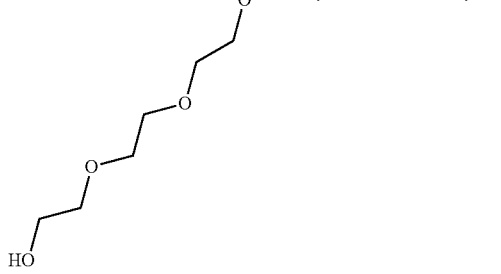
(3)-17
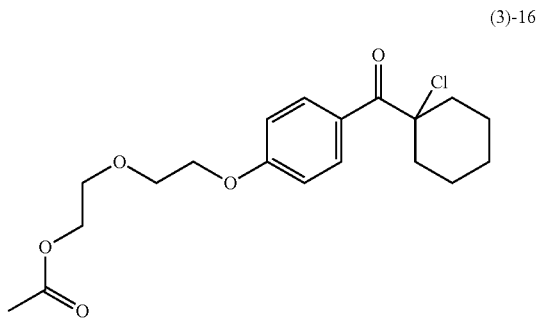
(3)-18
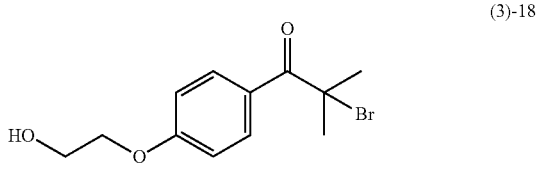

-continued (3)-19

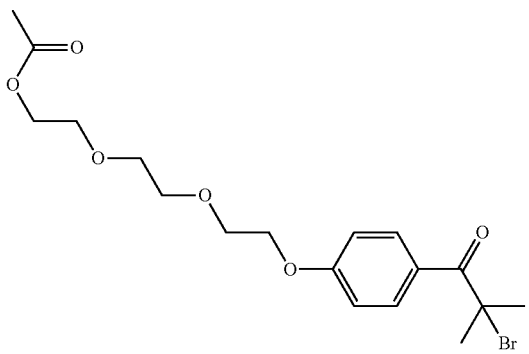

The α-halogenoacetophenon compound represented by Formula (3) is particularly suitable as the synthetic intermediate of the photopolymerization initiator.

That is, the compound represented by Formula (5) below is obtained by reacting the α-halogenoacetophenon compound represented by Formula (3) and a base. It is preferable that the reaction is performed by adding water. The compound represented by Formula (5) can be suitably used as a photopolymerization initiator and particularly a radical polymerization initiator or a precursor thereof.

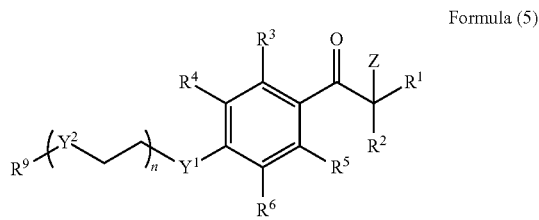

Formula (5)

In Formula (5), $R^1$ to $R^6$, $Y^1$, $Y^2$, and n have the same meaning as $R^1$ to $R^6$, $Y^1$, $Y^2$, and n in Formula (3) above respectively, and preferable embodiments thereof are also the same. If n is 2 or 3, the compound of Formula (5) has high water solubility and can be suitably used as an aqueous initiator.

$R^9$ represents a hydrogen atom, an alkyl group (an alkyl group having preferably 1 to 10 carbon atoms, more preferably 1 to 5 carbon atoms, and still more preferably 1 to 3 carbon atoms), an acyl group (an acyl group having preferably 2 to 10 carbon atoms, more preferably 2 to 6 carbon atoms, and still more preferably 2 to 4 carbon atoms), or a trialkylsilyl group (one alkyl group of the trialkylsilyl group has preferably 1 to 10 carbon atoms, more preferably 1 to 5 carbon atoms, and still more preferably 1 or 2 carbon atoms). Z represents a hydroxy group, an alkoxy group (an alkoxy group having preferably 1 to 10 carbon atoms, more preferably 1 to 5 carbon atoms, and still more preferably 1 to 3 carbon atoms) or an alkylamino group (including a dialkylamino group, and one alkyl group of the alkylamino group has preferably 1 to 10 carbon atoms, more preferably 1 to 5 carbon atoms, and still more preferably 1 to 3 carbon atoms).

Examples of the base include sodium hydroxide, potassium hydroxide, calcium hydroxide, lithium hydroxide, cesium hydroxide, rubidium hydroxide, sodium alkoxide (for example, sodium methoxide and sodium ethoxide), and alkyl amine.

For example, if reaction is performed by using sodium hydroxide as a base and adding a sodium hydroxide aqueous solution, Z in Formula (5) can be caused to be a hydroxyl group. In addition, in this case, if $R^7$ of Formula (3) is an acyl group, $R^7$ undergoes hydrolysis such that $R^9$ of Formula (5) becomes a hydrogen atom.

In addition, if sodium alkoxide is used as a base, Z in Formula (5) can be used as an alkoxy group.

In addition, if alkyl amine is used as a base, Z in Formula (5) can be used as an alkylamino group.

The usage amount of the base is preferably 1 to 50 and more preferably 5 to 20 as a molar ratio with respect to 1 of the α-halogenoacetophenon compound.

The reaction of the α-halogenoacetophenon compound represented by Formula (3) and the base is preferably performed by using a mixing solvent of water and a water soluble organic solvent. Examples of the water soluble organic solvent include glycerin, alkanediol (polyhydric alcohols) such as 1,2,6-hexanetriol, trimethylolpropane, ethylene glycol, and propylene glycol; sugar alcohols; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-isopropyl ether, diethylene glycol mono-isopropyl ether, ethylene glycol mono-n-butyl ether, ethylene glycol mono-t-butyl ether, diethylene glycol mono-t-butyl ether, triethylene glycol monoethyl ether, 1-methyl-1-methoxy butanol, propylene glycol monomethyl ether, propylene glycol monoethyl ether, propylene glycol mono-t-butyl ether, propylene glycol mono-n-propyl ether, propylene glycol mono-isopropyl ether, dipropylene glycol, dipropylene glycol monomethyl ether, dipropylene glycol monoethyl ether, dipropylene glycol mono-n-propyl ether, dipropylene glycol mono-isopropyl ether, and tripropylene glycol monomethyl ether. Among these, in view of volatile removability, alcohol having 1 to 4 carbon atoms (for example, one or more types selected from ethanol, methanol, butanol, propanol, and isopropanol) is preferably used.

The reaction of the α-halogenoacetophenon compound represented by Formula (3) and the base is preferably performed at 10° C. to 40° C. The reaction time of this reaction is preferably 0.5 hours to 5 hours.

The compound represented by Formula (5) that can be obtained by this reaction generally contains a certain amount of a brominated product as an impurity.

In Formula (5), specific examples of the compound in which Z is a hydroxy group are provided below, but the invention is not limited thereto.

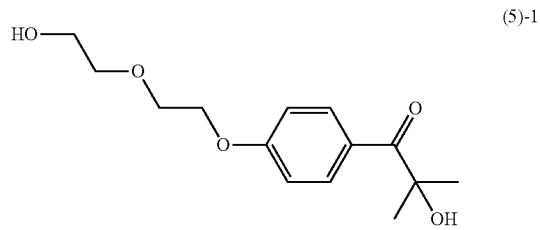

(5)-1

-continued

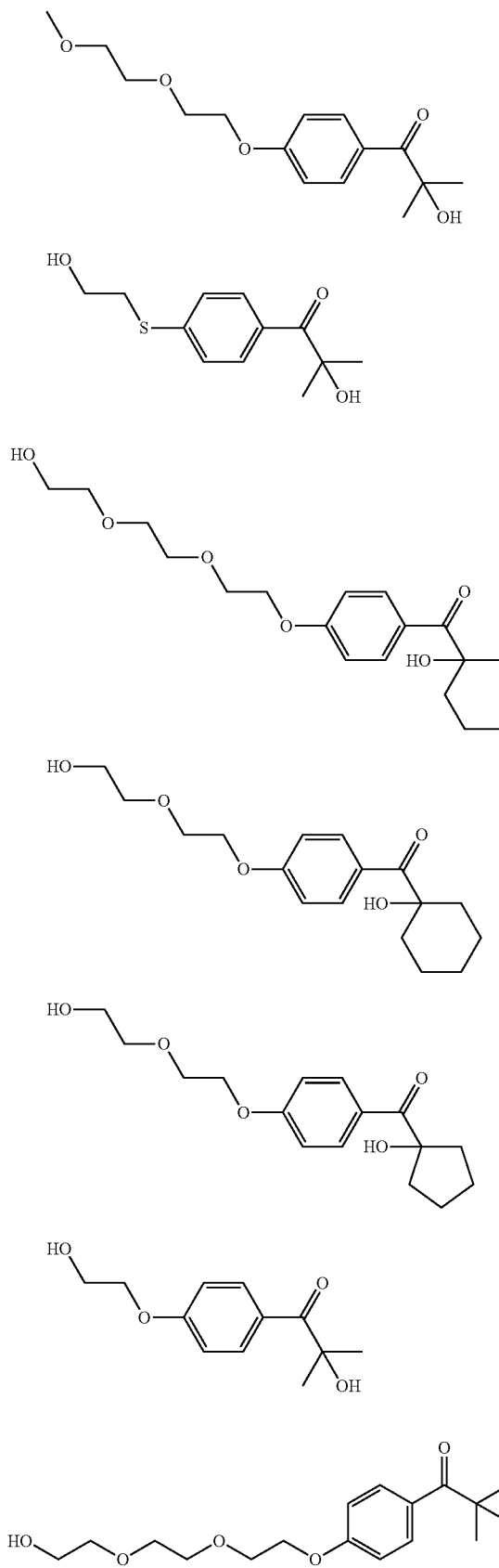

Hereinafter, the invention is more specifically described based on examples, but the invention is not limited thereto.

EXAMPLES

Reference Example 1

Scheme 1

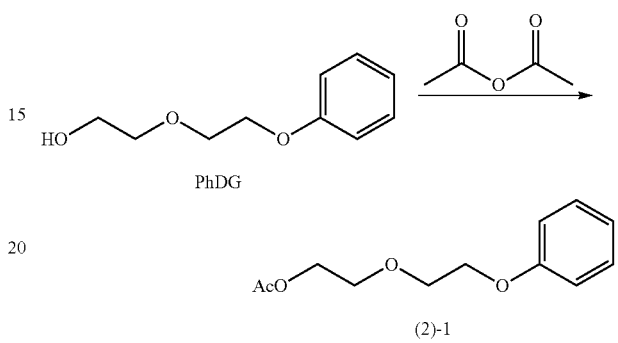

(Synthesis of Compound (2)-1)

97.2 g of acetic anhydride (0.95 mol) was added dropwise to 170.0 g of phenyl diglycol (PhDG, manufactured by Nippon Nyukazai Co., Ltd.) (0.93 mol) heated to 90° C., and heated and stirred at 120° C. for 6 hours. Thereafter, concentration was performed under a reduced pressure so as to obtain 204.4 g of a compound (2)-1 (98% yield).

$^1$H-NMR (CDCl$_3$)

δ: 2.10 (3H, s), 3.78 (2H, m), 3.87 (2H, m), 4.15 (2H, m), 4.26 (2H, m), 6.90-6.98 (3H, m), 7.25-7.32 (2H, m)

Example 1

Scheme 2

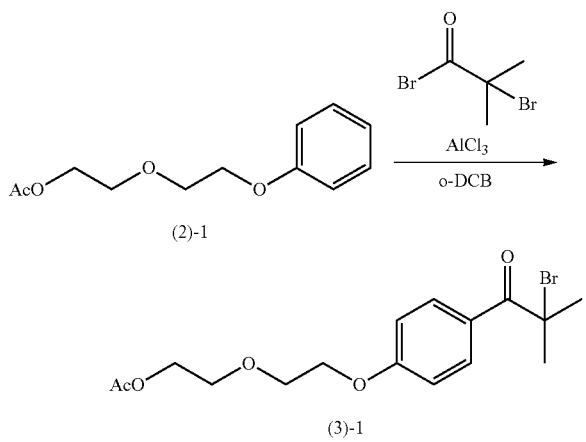

(Synthesis of Compound (3)-1)

120.0 g of aluminium (III) chloride (0.90 mol) was added to 270 mL of o-dichlorobenzene (2.39 mol) and cooled to 0° C. 44.26 mL of 2-bromoisobutyryl bromide (compound (1)-1) (0.36 mol) was added dropwise and stirred for 15 minutes. Thereafter, while the temperature of the reaction liquid was maintained to 0° C., 67.28 g of the compound (2)-1 (0.30 mol) obtained in Reference Example 1 above was added dropwise for 30 minutes. After the dropwise addition was completed, the temperature of the reaction liquid was cooled to room temperature (22° C.), and the reaction liquid was stirred for two hours. Thereafter, the reaction liquid was added to 300 mL of water cooled to 5° C. in several batches. After an organic phase was washed with 300 ml of water twice and further washed with 135 mL of a sodium bicarbonate aqueous solution and 135 mL of a saturated saline solution, 300 mL of water was added to the organic phase, and azeotropic concentration was performed under reduced pressure, so as to obtain 110.8 g of a compound (3)-1 (95% yield).

$^1$H-NMR (CDCl$_3$)

δ: 2.04 (6H, s), 2.08 (3H, s), 3.79 (2H, m), 3.85 (2H, m), 4.21 (2H, m), 4.26 (2H, m), 6.94 (2H, d), 8.21 (2H, d)

Comparative Example 1

Scheme 3

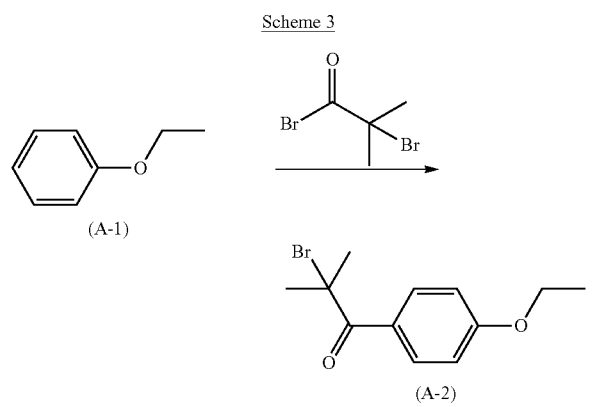

(Synthesis of Compound (A-2))

A compound (A-2) was synthesized in the same manner as in Example 1 except for using PHENETOLE (a compound (A-1), manufactured by Tokyo Chemical Industry Co., Ltd.) instead of the compound (2)-1 in Example 1.

Comparative Example 2

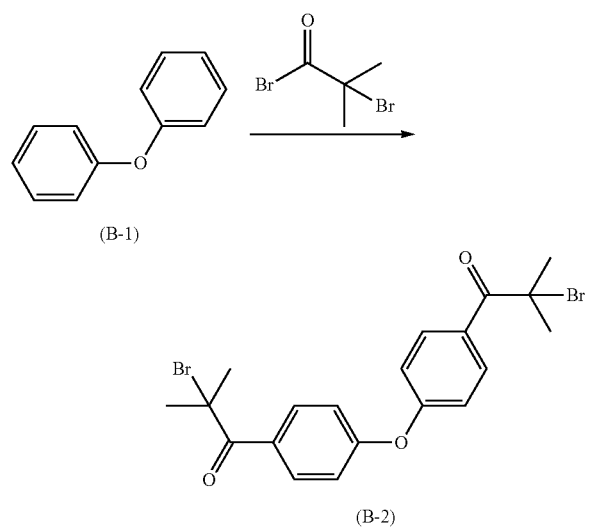

(Synthesis of the Compound (B-2))

A compound (B-2) was synthesized in the same manner as in Example 1 except for using diphenyl ether (a compound (B-1)) instead of the compound (2)-1 in Example 1.

Comparative Example 3

Scheme 5

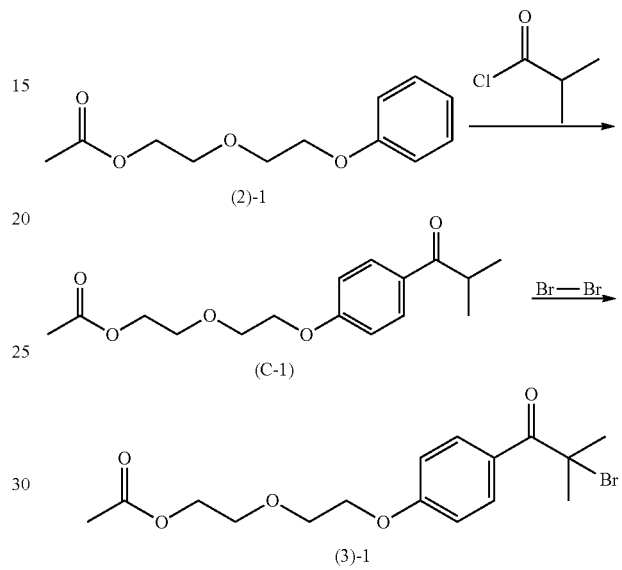

(Synthesis of Compound (C-1))

10.0 g of the compound (2)-1 (44.59 mmol) was dissolved in 40 mL of chlorobenzene, cooled to 5° C. in a cold bath, and 17.84 g of aluminium (III) chloride (133.78 mmol) was added thereto. Thereafter, 5.59 mL of isobutyric acid chloride (53.51 mmol) was added dropwise and stirred for one hour. Subsequently, this reaction liquid was poured to 80 g of ice, and the reaction product was extracted with 40 mL of ethyl acetate. The organic phase was washed with 80 ml of a sodium bicarbonate aqueous solution and 40 ml of a saline solution and dried by using 10 g of magnesium sulfate. After magnesium sulfate was filtered and removed, the filtrate was concentrated under reduced pressure, so as to obtain 11.87 g of a compound (C-1) (90% yield).

$^1$H-NMR (CDCl$_3$)

δ: 1.20 (3H, s), 1.21 (3H, s), 2.10 (3H, s), 3.52 (1H, m), 3.78 (2H, m), 3.89 (2H, m), 4.20 (2H, m), 4.27 (2H, m), 6.97 (2H, d), 7.95 (2H, d)

(Synthesis of Compound (3)-1)

10.0 g of the compound (C-1) (0.034 mol) obtained above was dissolved in 20 mL of glacial acetic acid, 5.7 g of bromine (0.036 mol) was added dropwise, and stirring was performed for 30 minutes. Further, 7 mL of a 3-wt % sodium hydrogen sulfite aqueous solution was added dropwise to the solution after stirring, the reaction liquid was washed with a sodium hydrogen carbonate aqueous solution and a saturated saline solution. After drying was performed with magnesium sulfate, magnesium sulfate was filtrated and removed, and the filtrate was concentrated under reduced pressure, so as to obtain 11.6 g of the compound (3)-1 (91% yield).

23

Comparative Example 4

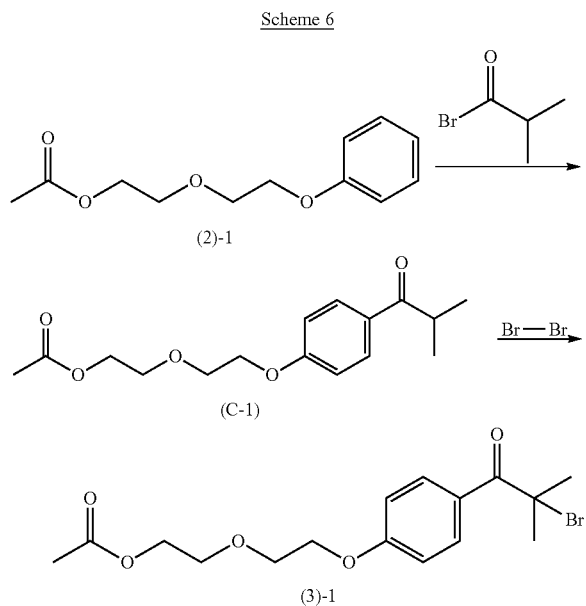

The compound (3)-1 was synthesized in the same manner as in Comparative Example 3 except for using isobutyryl bromide instead of isobutyric acid chloride in Comparative Example 3.

[Purity Analysis]

The compounds (3)-1 obtained in Example 1, Comparative Example 3, and Comparative Example 4, the compound (A-2) obtained in Comparative Example 1, and the compound (B-2) obtained in Comparative Example 2 were analyzed in the condition below by using liquid chromatography (HPLC (CLASS-VP) manufactured by Shimadzu Corporation), so as to determine a quantity of purity of each compound. This purity becomes indexes of regioselectivity of an acylation and regioselectivity of a bromination. Results thereof are provided below in Table 1.

(Conditions of Liquid Chromatography)

Column: 5 μm of Type AQ manufactured by SHISEIDO Co., Ltd. (Size) 4.6 mmI.D.×250 mm Sample preparation: 10 mg of Sample/10 ml of MeOH for HPLC Injection amount: 10

Eluent: A: MeOH/$H_2O$=1/9 0.1% $AcONH_4$

B: MeOH/$H_2O$=9/1 0.1% $AcONH_4$

Detection wavelength: 270 nm

Time program:

| Time [min] | B Liquid ratio (vol %) |
|---|---|
| 0 | 35 |
| 30 | 35 |
| 40 | 100 |
| 50 | 100 |
| 60 | 35 |

24

TABLE 1

| | Yield (%) | Purity (HPLC area %) |
|---|---|---|
| Example 1 | 95 | 98 |
| Comparative Example 1 | — | 78 |
| Comparative Example 2 | — | 65 |
| Comparative Example 3 | 82 | 79 |
| Comparative Example 4 | 73 | 75 |

As presented in Table 1 above, in case α-halogenocarboxylic halide included in Formula (1) was used as an acylating agent, if PHENETOLE or diphenyl ether that is not included in Formula (2) is used as a phenyl compound, the purity of the obtained desired acylated compound (compound in which para position of the substituent of a reactant was acylated) was low (Comparative Examples 1 and 2).

In addition, in case the compound (3)-1 (the compound of Formula (3)) was obtained through bromination after acylation using isobutyric acid chloride or isobutyryl bromide as an acylating agent, purity of the compound (3)-1 was deteriorated (Comparative Examples 3 and 4).

In contrast, if the compound (3)-1 was synthesized in the producing method according to the invention, the yield of the compound (3)-1 was 95% and purity was 98%, and both of the yield and the purity were excellent (Example 1). In this result, it was found that the α-halogenoacetophenon compound of Formula (3) was manufactured with high efficiency in the producing method according to the invention, with fewer steps.

The reason for deteriorating the purity of the compounds (3)-1 in Comparative Examples 3 and 4 is not clear, but it is considered that it is because a compound below in which a bromine atom was introduced to an aromatic ring in a bromination step was produced.

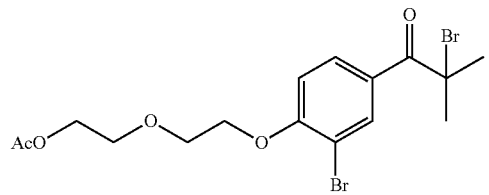

In addition, according to the comparison between Comparative Examples 3 and 4 above, it was found that, in a reaction scheme in which bromination reaction was performed after acylation, when isobutyric acid chloride was used, the yield and the purity of the desired product were higher than a case where isobutyryl bromide was used as an acylating agent.

Synthetic Example 1

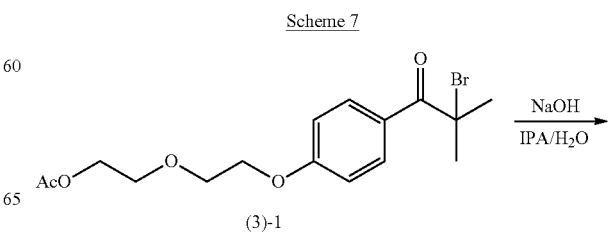

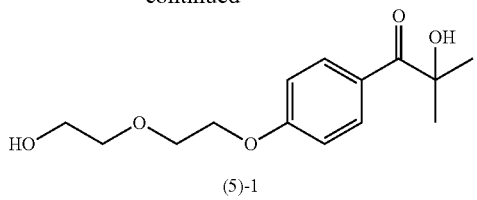

(5)-1

(Synthesis of Compound (5)-1)

100.0 g of the compound (3)-1 (0.27 mol) which was obtained in the same manner as in Example 1 was dissolved in 200 mL of isopropanol, 214 g of a 25-wt % sodium hydroxide aqueous solution was added dropwise, and stirring was performed for two hours. Thereafter, the stirring was stopped, the reaction liquid was washed with a saturated saline solution twice, and neutralization was performed with a hydrochloric acid. After the reaction liquid was concentrated under reduced pressure, 72 mL of methyl ethyl ketone was added thereto, and a precipitated salt was filtrated. After the filtrate was concentrated under reduced pressure, 72 mL of water was added thereto, and then azeotropic concentration was performed under reduced pressure, so as to obtain 56.8 g of the compound (5)-1 (87% yield).

$^1$H-NMR (CDCl$_3$)

δ: 1.64 (6H, s), 3.69 (2H, m), 3.78 (2H, m), 3.91 (2H, m), 4.22 (2H, m), 4.26 (1H, s), 6.97 (2H, d), 8.06 (2H, d)

The purity of the compound (5)-1 was calculated based on a peak area ratio of HPLC and was 98%. In addition, in the compound (5)-1, the content of a bromide ion which is an impurity was calculated with ion chromatography and was 21 ppm (in terms of mass).

Synthetic Example 2

Scheme 8

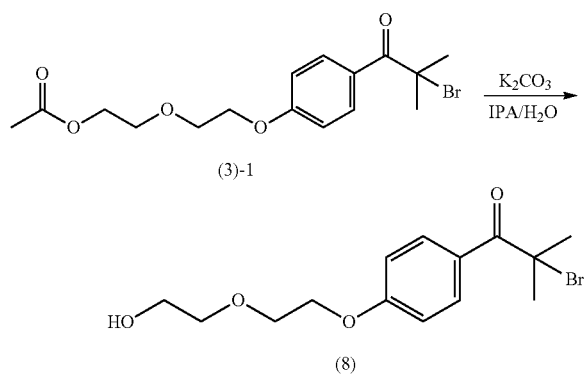

(Synthesis of the Compound (8))

100.0 g of the compound (3)-1 (0.27 mol) which can be obtained in the same manner as in Example 1 was dissolved in 200 mL of isopropanol and 100 mL of methanol, 186 g of potassium carbonate was added thereto in small batches, and stirring was performed for two hours. After the reaction liquid was filtrated, the organic phase was washed twice in the saturated saline solution. Thereafter, the organic phase was concentrated under reduced pressure, and 72 mL of methyl ethyl ketone was added. A precipitated salt was filtrated, the filtrate was concentrated under reduced pressure and the product was purified with column chromatography, so as to obtain 45.6 g of a compound (8) (51% yield).

$^1$H-NMR (CDCl$_3$)

δ:2.03 (6H, s), 3.68 (2H, m), 3.75 (2H, m), 3.95 (2H, m), 4.21 (2H, m), 4.23 (1H, s), 7.07 (2H, d), 8.12 (2H, d)

Examples 2 to 28 and Comparative Examples 5 to 7

The compound (3)-1 was synthesized (a compound number in Tables 2-1 and 2-2 below corresponds to a number of the compound described above) in the same manner as in Example 1 except for using the reaction condition presented in Table 2 below instead of the reaction condition of Example 1. Here, in Examples 4, 5, and 13 to 16, and Comparative Example 5, the molar ratio of the Lewis acid and the phenyl compound of Formula (2) was adjusted by adjusting the additive amount of aluminium chloride (III). The purity of the obtained compound (3)-1 was calculated based on a peak area ratio of HPLC in the same manner as above. Results thereof are provided in Tables 2-1 and 2-2 below.

In addition, the compound (5)-1 was synthesized in the same manner as in Synthetic Example 1 by using the compounds (3)-1 obtained in Examples 2 to 28 and Comparative Examples 5 to 7, so as to measure the purity of each of the obtained compounds. Results thereof are also presented in Tables 2-1 and 2-2 below.

The temperature of dropwise addition in Tables 2-1 and 2-2 are temperature of the liquid (reaction liquid) including the solvent, which receives dripped liquid.

In addition, in Example 17 of Table 2-1, aluminium (III) chloride which is the Lewis acid was added in small batches.

In addition, in Comparative Example 7, acylation was performed in the same manner as in Example 1 except that benzene as the phenyl compound was used in the same molar amount as the compound (2)-1 in Example 1 instead of the compound (2)-1, and the reaction condition was changed to the condition represented in Table 2 below.

In addition, the bromine atom of the obtained acylated benzene was substituted with a hydroxy group in the same manner as in Synthetic Example 1. In Table 2-2, "purity of the compound (3)-1" in the section of Comparative Example 7 indicates the purity of the monoacylated benzene and "purity of the compound (5)-1" indicates the purity of the hydroxy substituted compound of the monoacylated benzene.

TABLE 2-1

| | Compound of Formula (1) | Lewis acid | Compound of Formula (2) | Solvent | Lewis acid/ Formula (2) (Molar ratio) | Temperature of dropwise addition (° C.) | Solvent/ Formula (2) (Molar ratio) | Sequence of addition to solvent | Yield (%) of Compound (3)-1 | Purity of Compound (3)-1 (HPLC area %) | Purity of Compound (5)-1 (HPLC area %) |
|---|---|---|---|---|---|---|---|---|---|---|---|
| Example 1 | (1)-1 | AlCl$_3$ | (2)-1 | o-dichlorobenzene | 3.0 | 0 | 7.96 | Lewis acid → (1)-1 → (2)-1 | 95 | 98 | 98 |
| Example 2 | (1)-1 | AlCl$_3$ | (2)-1 | o-dichlorobenzene | 3.0 | 20 | 7.96 | Lewis acid → (1)-1 → (2)-1 | 95 | 98 | 98 |

TABLE 2-1-continued

| | Compound of Formula (1) | Lewis acid | Compound of Formula (2) | Solvent | Lewis acid/ Formula (2) (Molar ratio) | Temperature of dropwise addition (° C.) | Solvent/ Formula (2) (Molar ratio) | Sequence of addition to solvent | Yield (%) of Compound (3)-1 | Purity of Compound (3)-1 (HPLC area %) | Purity of Compound (5)-1 (HPLC area %) |
|---|---|---|---|---|---|---|---|---|---|---|---|
| Example 3 | (1)-1 | AlCl$_3$ | (2)-1 | o-dichlorobenzene | 3.0 | 10 | 7.96 | Lewis acid → (1)-1 → (2)-1 | 95 | 99 | 99 |
| Example 4 | (1)-1 | AlCl$_3$ | (2)-1 | o-dichlorobenzene | 2.5 | 0 | 7.96 | Lewis acid → (1)-1 → (2)-1 | 95 | 96 | 96 |
| Example 5 | (1)-1 | AlCl$_3$ | (2)-1 | o-dichlorobenzene | 3.5 | 0 | 7.96 | Lewis acid → (1)-1 → (2)-1 | 95 | 99 | 99 |
| Example 6 | (1)-1 | AlCl$_3$ | (2)-1 | o-dichlorobenzene | 3.0 | 50 | 7.96 | Lewis acid → (1)-1 → (2)-1 | 95 | 96 | 96 |
| Example 7 | (1)-1 | AlCl$_3$ | (2)-1 | o-dichlorobenzene | 3.0 | 40 | 7.96 | Lewis acid → (1)-1 → (2)-1 | 90 | 97 | 97 |
| Example 8 | (1)-1 | AlCl$_3$ | (2)-1 | o-dichlorobenzene | 3.0 | 30 | 7.96 | Lewis acid → (1)-1 → (2)-1 | 95 | 98 | 98 |
| Example 9 | (1)-1 | AlCl$_3$ | (2)-1 | o-dichlorobenzene | 3.0 | −15 | 7.96 | Lewis acid → (1)-1 → (2)-1 | 92 | 96 | 96 |
| Example 10 | (1)-1 | AlCl$_3$ | (2)-1 | o-dichlorobenzene | 3.0 | 0 | 12 | Lewis acid → (1)-1 → (2)-1 | 95 | 97 | 97 |
| Example 11 | (1)-1 | AlCl$_3$ | (2)-1 | o-dichlorobenzene | 3.0 | 0 | 5 | Lewis acid → (1)-1 → (2)-1 | 94 | 96 | 96 |
| Example 12 | (1)-1 | AlCl$_3$ | (2)-1 | o-dichlorobenzene | 3.0 | 0 | 15 | Lewis acid → (1)-1 → (2)-1 | 95 | 96 | 96 |
| Example 13 | (1)-1 | AlCl$_3$ | (2)-1 | o-dichlorobenzene | 2.0 | 0 | 7.96 | Lewis acid → (1)-1 → (2)-1 | 90 | 90 | 90 |
| Example 14 | (1)-1 | AlCl$_3$ | (2)-1 | o-dichlorobenzene | 4.0 | 0 | 7.96 | Lewis acid → (1)-1 → (2)-1 | 95 | 99 | 99 |
| Example 15 | (1)-1 | AlCl$_3$ | (2)-1 | o-dichlorobenzene | 6.0 | 0 | 7.96 | Lewis acid → (1)-1 → (2)-1 | 95 | 99 | 99 |
| Example 16 | (1)-1 | AlCl$_3$ | (2)-1 | o-dichlorobenzene | 5.0 | 0 | 7.96 | Lewis acid → (1)-1 → (2)-1 | 95 | 99 | 99 |
| Example 17 | (1)-1 | AlCl$_3$ | (2)-1 | o-dichlorobenzene | 3.0 | 20 | 7.96 | (2)-1 → Lewis acid → (1)-1 | 92 | 90 | 90 |
| Example 18 | (1)-1 | AlCl$_3$ | (2)-1 | methylene chloride | 3.0 | 20 | 7.96 | Lewis acid → (1)-1 → (2)-1 | 89 | 97 | 97 |
| Example 19 | (1)-1 | AlCl$_3$ | (2)-1 | methylene chloride | 3.0 | 10 | 7.96 | Lewis acid → (1)-1 → (2)-1 | 90 | 97 | 97 |
| Example 20 | (1)-1 | AlCl$_3$ | (2)-1 | methylene chloride | 3.0 | −15 | 7.96 | Lewis acid → (1)-1 → (2)-1 | 90 | 96 | 96 |

TABLE 2-2

| | Compound of Formula (1) | Lewis acid | Compound of Formula (2) | Solvent | Lewis acid/ Formula (2) (Molar ratio) | Dripping temperature (° C.) | Solvent/ Formula (2) (Molar ratio) | Dripping sequence to solvent | Yield (%) of Compound (3)-1 | Purity of Compound (3)-1 (HPLC area %) | Purity of Compound (5)-1 (HPLC area %) |
|---|---|---|---|---|---|---|---|---|---|---|---|
| Example 21 | (1)-1 | AlCl$_3$ | (2)-1 | methylene chloride | 3.0 | 0 | 12 | Lewis acid → (1)-1 → (2)-1 | 91 | 95 | 95 |
| Example 22 | (1)-1 | AlCl$_3$ | (2)-1 | methylene chloride | 3.0 | 0 | 5 | Lewis acid → (1)-1 → (2)-1 | 91 | 97 | 97 |
| Example 23 | (1)-1 | AlCl$_3$ | (2)-1 | methylene chloride | 3.0 | 0 | 15 | Lewis acid → (1)-1 → (2)-1 | 91 | 96 | 96 |
| Example 24 | (1)-1 | AlCl$_3$ | (2)-1 | ethyl acetate | 2.5 | 20 | 7.96 | Lewis acid → (1)-1 → (2)-1 | 71 | 90 | 90 |
| Example 25 | (1)-1 | AlCl$_3$ | (2)-1 | chlorobenzene | 3.5 | 20 | 7.96 | Lewis acid → (1)-1 → (2)-1 | 75 | 91 | 91 |
| Example 26 | (1)-1 | AlCl$_3$ | (2)-1 | acetonitrile | 3.0 | 20 | 7.96 | Lewis acid → (1)-1 → (2)-1 | 72 | 91 | 91 |
| Example 27 | (1)-1 | AlCl$_3$ | (2)-1 | methyl ethyl ketone | 3.0 | 20 | 7.96 | Lewis acid → (1)-1 → (2)-1 | 71 | 91 | 90 |
| Example 28 | (1)-1 | AlCl$_3$ | (2)-1 | sulfolane | 3.0 | 20 | 7.96 | Lewis acid → (1)-1 → (2)-1 | 71 | 90 | 90 |
| Comparative Example 5 | (1)-1 | AlCl$_3$ | (2)-1 | o-dichlorobenzene | 1.5 | 20 | 7.96 | Lewis acid → (1)-1 → (2)-1 | 38 | 44 | 44 |
| Comparative Example 6 | (1)-1 | AlCl$_3$ | (2)-1 | none | 3.0 | 20 | 12 | Lewis acid → (1)-1 → (2)-1 | 12 | 4 | 4 |
| Comparative Example 7 | (1)-1 | AlCl$_3$ | Benzene | methylene chloride | 3.0 | 20 | 5 | Lewis acid → (1)-1 → (2)-1 | 93 | 23 | 23 |

From Tables 2-1 and 2-2, if the ratio of the Lewis acid to the phenyl compound is smaller than the value regulated in the invention, the acylation reaction was not be completed, and the amount of the product in which an acyl group was introduced in the para position to the polar group (EO chain) greatly decreased (Comparative Example 5).

In addition, when the solvent was not used, the material was solidified and the reaction did not progress, and the amount of the product in which the acyl group was introduced in the para position to the polar group (EO chain) was extremely small (Comparative Example 6).

In addition, in Comparative Example 7 in which benzene without a polar group was used as the phenyl compound, 23% of the compound in which one acyl group was introduced to one benzene molecular was included, a mixture product including a considerable amount of the compound in which three or more acyl groups were introduced in one benzene molecular, in addition to a compound in which two acyl groups were introduced to one benzene molecular and a compound in which an acyl group was not introduced to a benzene ring.

In contrast, in the producing method of the embodiment, the compound (3)-1 to which an acyl group was introduced in the para position of the polar group (EO chain) was able to be obtained with high purity at a high yield (Examples 1 to 28). In addition, it was found that purity further increased by using o-dichlorobenzene or methylene chloride as the solvent.

Examples 29 to 37

In addition, the compound of Formula (3) was synthesized in the same manner as in Example 1 (a compound number in Table 3 below corresponds to a number of the compound described above) except for using compounds presented in Table 3 below instead of the compound of Formula (1) and the compound of Formula (2) used in Example 1. The purity of the obtained compound of Formula (3) was measured in the same manner as above. The results are presented in Table 3 below. In addition, all of the compounds (3)-1, (3)-12, (3)-15, (3)-17, and (3)-19 were liquid at 5° C. to 30° C.

In addition, the compounds of Formula (5) were synthesized in the same manner as in Synthetic Example 1 using the compounds of Formula (3) which were obtained in Examples 29 to 37 and the purity thereof was measured. Results thereof are presented in Table 3 below.

From the results of Table 3, it was found that an acyl group derived from the α-halogenocarboxylic halide compound was able to be introduced to the phenyl compound having a specific polar group in the producing method according to the invention, under the moderate temperature condition with high para (the para position to the polar group) selectivity.

In addition, in the producing method according to the invention, in case the same reactant compounds was used, a case where α-halogenocarboxylic bromide was used as an acylating agent had an effect of the more excellent yield than a case where α-halogenocarboxylic chloride was used (comparison of Example 1 with Examples 29, 32, and 35, and comparison of Example 36 and Example 37). That is, a tendency which is reverse to a tendency in a reaction scheme (that is, a reaction scheme of Comparative Examples 3 and 4) in the related art in which bromination reaction after acylation is performed was exhibited.

Further, in case the same acylating agent was used, a case of using a compound of Formula (2) in which n is 2 exhibited a more excellent result in both of the yield and the purity, than a case of using a compound of Formula (2) in which n is 1, as the reactant (comparison of Examples 30 and 36 with Example 1, and comparison of Example 37 and Example 29).

What is claimed is:

1. A method for producing an α-halogenoacetophenon compound represented by Formula (3) below, comprising:
reacting an α-halogenocarboxylic halide compound represented by Formula (1) below and a phenyl compound represented by Formula (2) in the presence of a Lewis acid in a solvent,
wherein the α-halogenocarboxylic halide compound and the phenyl compound are reacted with each other in a molar ratio of the Lewis acid to the phenyl compound represented below, 2≤Lewis acid/phenyl compound≤6

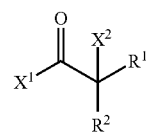

Formula (1)

in Formula (1), each of $R^1$ and $R^2$ independently represents an alkyl group, $X^1$ represents a halogen atom, and $X^2$ represents a bromine atom,

TABLE 3

| | Compound of Formula (1) | Compound of Formula (2) | Compound of Formula (3) | Compound of Formula (5) | Yield of compound of Formula (3) (%) | Purity of compound of Formula (3) (HPLC area %) | Purity of compound of Formula (5) (HPLC area %) |
|---|---|---|---|---|---|---|---|
| Example 1 | (1)-1 | (2)-1 | (3)-1 | (5)-1 | 95 | 98 | 98 |
| Example 29 | (1)-9 | (2)-1 | (3)-1 | (5)-1 | 80 | 95 | 95 |
| Example 30 | (1)-1 | (2)-10 | (3)-5 | (5)-7 | 84 | 90 | 90 |
| Example 31 | (1)-1 | (2)-11 | (3)-19 | (5)-8 | 90 | 97 | 97 |
| Example 32 | (1)-3 | (2)-1 | (3)-16 | (5)-5 | 73 | 94 | 94 |
| Example 33 | (1)-7 | (2)-2 | (3)-12 | (5)-2 | 87 | 96 | 96 |
| Example 34 | (1)-3 | (2)-5 | (3)-15 | (5)-4 | 72 | 94 | 94 |
| Example 35 | (1)-4 | (2)-1 | (3)-17 | (5)-6 | 72 | 96 | 96 |
| Example 36 | (1)-1 | (2)-9 | (3)-18 | (5)-7 | 80 | 91 | 91 |
| Example 37 | (1)-9 | (2)-9 | (3)-18 | (5)-7 | 75 | 90 | 90 |

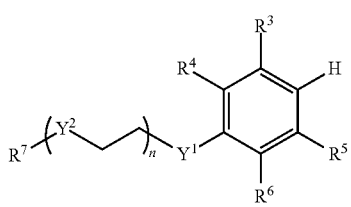

Formula (2)

in Formula (2), each of $R^3$ to $R^6$ independently represents a hydrogen atom, $R^7$ represents a hydrogen atom, an alkyl group, an acyl group, or a trialkylsilyl group, each of $Y^1$ and $Y^2$ independently represents an oxygen atom, and n represents 2, and

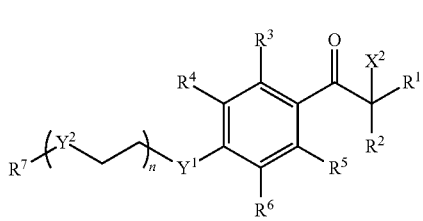

Formula (3)

in Formula (3), $R^1$, $R^2$, and $X^2$ respectively have the same meanings as $R^1$, $R^2$, and $X^2$ in Formula (1), and $R^3$ to $R^7$, $Y^1$, $Y^2$, and n respectively have the same meanings as $R^3$ to $R^7$, $Y^1$, $Y^2$, and n in Formula (2).

2. The method for producing an α-halogenoacetophenon compound according to claim 1,
wherein, in Formula (1), $X^1$ represents a bromine atom.

3. The method for producing an α-halogenoacetophenon compound according to claim 2,
wherein, in Formula (1), $R^1$ and $R^2$ are methyl.

4. The method for producing an α-halogenoacetophenon compound according to claim 1,
wherein aluminium (III) chloride is used as the Lewis acid.

5. The method for producing an α-halogenoacetophenon compound according to claim 1,
wherein $R^7$ in Formulae (2) and (3) is an alkylcarbonyl group or an arylcarbonyl group.

6. The method for producing an α-halogenoacetophenon compound according to claim 1,
wherein at least one selected from dichloromethane, chlorobenzene, sulfolane, ethyl acetate, acetonitrile, 1,3,5-trimethylbenzene, methyl ethyl ketone, and o-dichlorobenzene is used as the solvent.

7. The method for producing an α-halogenoacetophenon compound according to claim 1,
wherein, at least one selected from dichloromethane, chlorobenzene, and o-dichlorobenzene is used as the solvent.

8. The method for producing an α-halogenoacetophenon compound according to claim 2,
wherein, at least one selected from dichloromethane, chlorobenzene, and o-dichlorobenzene is used as the solvent.

9. The method for producing an α-halogenoacetophenon compound according to claim 1,
wherein o-dichlorobenzene is used as the solvent.

10. The method for producing an α-halogenoacetophenon compound according to claim 2,
wherein o-dichlorobenzene is used as the solvent.

11. The method for producing an α-halogenoacetophenon compound according to claim 9,
wherein the α-halogenocarboxylic halide compound and the phenyl compound are reacted with each other in a molar ratio of the o-dichlorobenzene to the phenyl compound represented below 5≤o-dichlorobenzene/phenyl compound≤20.

12. The method for producing an α-halogenoacetophenon compound according to claim 10,
wherein the α-halogenocarboxylic halide compound and the phenyl compound are reacted with each other in a molar ratio of the o-dichlorobenzene to the phenyl compound represented below 5≤o-dichlorobenzene/phenyl compound≤20.

13. The method for producing an α-halogenoacetophenon compound according to claim 9,
wherein aluminium (III) chloride as the Lewis acid and the α-halogenocarboxylic halide compound are mixed with each other, in the o-dichlorobenzene, and
the phenyl compound is subsequently mixed.

14. The method for producing an α-halogenoacetophenon compound according to claim 1,
wherein the α-halogenocarboxylic halide compound and the phenyl compound are reacted under a temperature condition of 30° C. or lower.

15. An α-bromoacetophenon compound represented by Formula (6) below,

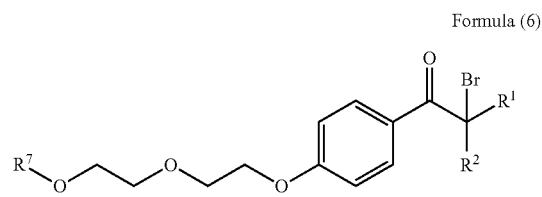

Formula (6)

wherein, in Formula (6), each of $R^1$ and $R^2$ independently represents an alkyl group, and $R^7$ represents a hydrogen atom, an alkyl group, an acyl group, or a trialkylsilyl group.

16. The α-bromoacetophenon compound according to claim 15,
wherein, in Formula (6), $R^1$ and $R^2$ are methyl, and $R^7$ is a hydrogen atom or acetyl.

* * * * *